United States Patent [19]

Graves

[11] Patent Number: 4,829,009
[45] Date of Patent: May 9, 1989

[54] NOISE CONTROLLED IMMUNOASSAYS

[75] Inventor: Howard Graves, Albany, Calif.

[73] Assignee: The Regents of the University of California, Berkeley, Calif.

[21] Appl. No.: 831,610

[22] Filed: Feb. 21, 1986

[51] Int. Cl.[4] .................. G01N 33/53; G01N 33/543; G01N 33/545

[52] U.S. Cl. .................. 436/518; 436/531; 436/807; 436/809; 436/825

[58] Field of Search ............... 436/825, 518, 531, 807, 436/809

[56] References Cited

U.S. PATENT DOCUMENTS

| | | | |
|---|---|---|---|
| 4,357,310 | 11/1982 | Chan | 436/504 X |
| 4,357,311 | 11/1982 | Schutt | 436/532 X |
| 4,518,701 | 5/1985 | Khanna | 436/825 X |
| 4,582,791 | 4/1986 | Khanna | 436/825 X |

OTHER PUBLICATIONS

Chemical Abstracts 105:221956e (1986).
"Laboratory Techniques in Biochemistry and Molecular Biology", T. S. Work et al., eds., vol. 6, part 2, pp. 17, 19.
Medical World News (Aug. 26, 1985) p. 15.
Prentice et al., (Aug. 3, 1985) Lancet p. 274–275.
Annals of Internal Medicine (1985) 103:791–795.
Livesey et al., (1982) Clinica Chimica Acta 123:193–198.
Hashida et al., (1983) Clinica Chimica Acta 135:263–273.
Bell et al., (1984) Biophys. J. 45:1051–1064.
Mehrishi in *Progress in Biophysics and Molecular Biology* (Butler, J. A. et al., ed. 1972)25:3–69.
Seno et al., (1983) Biorheology 20:653–662.
Brenner et al., (1978) Am. J. Physiol. 234:F455–F460.

*Primary Examiner*—Sidney Marantz
*Attorney, Agent, or Firm*—Irell & Manella

[57] ABSTRACT

A method for reducing false positives and to assay background noise in solid phase immunoassays utilizes a matrix coated on a solid support, which matrix contains an effective amount of a noise reduction component and an effective amount of noise balancing component. Optimization of the matrix composition is obtained by measuring parameters for its effectiveness which include sensitivity ratio, noise balance ratio, and signal to noise ratio.

31 Claims, 7 Drawing Sheets

FIG. 2

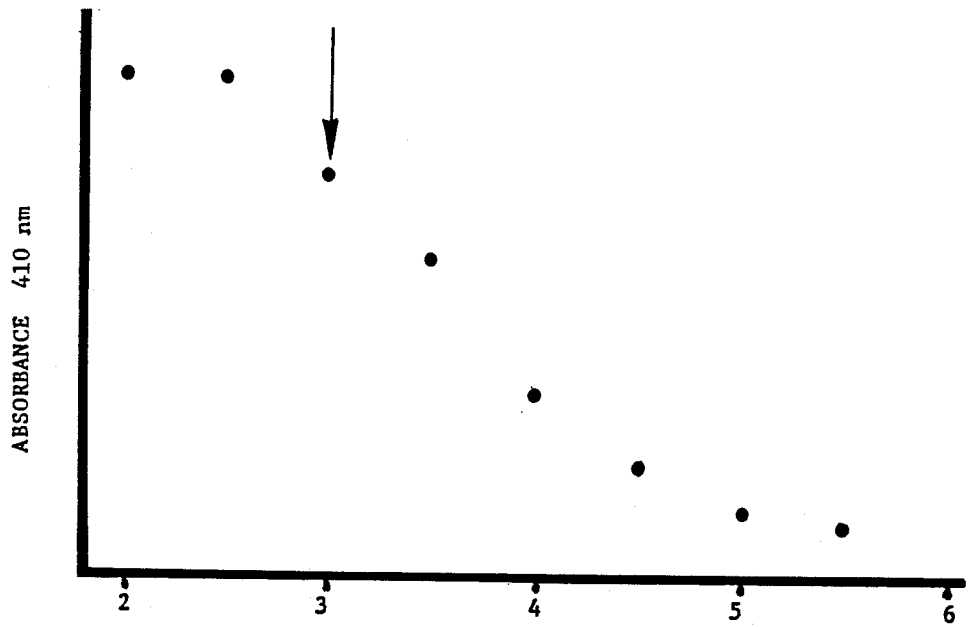

Log of Serum Dilution$^{-1}$

ELISA for anti-p30 IgG (rabbit)

Coat: p30 1µg/ml
Block: phosphate buffered saline with 0.05% Tween 20
Sample: Dilution of anti-p30 immune rabbit serum.
Detecting antibody: Alkaline phosphatase labelled goat antibody specific for rabbit IgG.
Method: see Example 1.

Arrow ➝ indicates the antiserum dilution selected as the optimal dilution for use as the antigen-specific signal probe. (i.e., optimal dilution = $\frac{1}{1000}$ )

FIG. 3

BSA (μg/ml)

| AGP (μg/ml) | | 0 | | 4 | | 8 | |
|---|---|---|---|---|---|---|---|
| | | i | n | i | n | i | n |
| 0 | m+a | 2.00 | 0.39 | 1.61 | 0.26 | 1.37 | 0.28 |
| | m | 0.00 | 0.16 | 0.00 | 0.24 | 0.00 | 0.41 |
| 5 | m+a | 1.72 | 0.23 | 1.47 | 0.17 | 1.48 | 0.26 |
| | m | 0.00 | 0.11 | 0.00 | 0.18 | 0.00 | 0.29 |
| 10 | m+a | 1.69 | 0.17 | 1.55 | 0.17 | 1.63 | 0.31 |
| | m | 0.00 | 0.12 | 0.00 | 0.17 | 0.00 | 0.29 | a = p30 (1 μg/ml)

FIG. 4

μg/ml BSA

| μg/ml AGP | 0 | 4 | 8 | |
|---|---|---|---|---|
| 0 | 1.0 | 0.80 | 0.68 | SR |
| | 5.1 | 6.2 | 4.9 | (S/N)R |
| | 0.41 | 0.92 | 0.68 | NBR |
| | (2.10) | (4.60) | (2.29) | MI |
| 5 | 0.86 | 0.73 | 0.74 | SR |
| | 7.5 | 8.64 | 5.7 | (S/N)R |
| | 0.48 | 0.94 | 0.90 | NBR |
| | (3.08) | (6.00) | (3.78) | MI |
| 10 | 0.85 | 0.78 | 0.81 | SR |
| | 9.9 | 9.1 | 5.3 | (S/N)R |
| | 0.71 | 1.00 | 0.94 | NBR |
| | (5.93) | (7.07) | (4.01) | MI |

Legend:  SR = sensitivity ratio
(S/N)R - signal to noise ratio
NBR - noise balance ratio
MI - matrix index

FIG. 8

HSA (µg/ml)

|  | 0 | | 2 | | 4 | | 6 | | 8 | |
|---|---|---|---|---|---|---|---|---|---|---|
|  | i | n | i | n | i | n | i | n | i | n |
| m+a | 1.97 | 0.55 | 1.96 | 0.49 | 1.93 | 0.49 | 1.96 | 0.50 | 1.93 | 0.58 |
| m | 0.02 | 0.19 | 0.02 | 0.32 | 0.02 | 0.39 | 0.02 | 0.51 | 0.02 | 0.53 |

| NBR | 0.35 | 0.65 | 0.80 | 0.98 | 0.91 |
| MI | 1.22 | 2.57 | 3.04 | 3.78 | 2.95 |

AGP = 10 µg/ml      p30 = 1 µg/ml

NOISE CONTROLLED IMMUNOASSAYS

This invention was made with Government support under Grant No.: SO7RR5441-2 with the National Institutes of Health and the University of California. The Government has certain rights in this invention.

TECHNICAL FIELD

The invention relates to immunological testing using solid phase immunoassay. More particularly, the invention relates to methods and materials to obviate false positives and permit decrease of and quantitation of background noise in such assays.

BACKGROUND ART

Over ten million solid phase immunoassays are run annually in the United States to detect the presence or absence of specific antibodies or antigens in biological samples, most commonly serum or urine. False positives in tests run in this manner are a common problem, and are sometimes so serious as to create a serious drawback to the use of the test. For example, recent efforts to screen blood samples for the presence of AIDS antibodies to certify blood available for transfusions have resulted in about 70% false positives on the initial screen (*Medical World News* (August 26, 1985) p. 15; Prentice, R. L. et al, *Lancet* (3 August 1985) p. 274–275). Furthermore, false positive results in screening for antibody to hepatitis B surface antigen threatens to undermine the usefulness of this test to screen patients for the costly hepatitis B vaccine (*Annals of Internal Medicine* (1985) 103:791–795). Elimination of false positives can generally be achieved through follow-up testing of positive samples using additional controls or different techniques. Although these approaches are expensive and time consuming, systematic internal noise control systems to eliminate false positives directly at the level of the initial assay have not been generally applied.

Some approaches to noise reduction associated with nonspecific binding of the test sample to the solid substrate in these assays have been applied, but these methods do not quantitatively account for the nonspecific binding. For example, Bullock, S. L. et al (*J Infect Disease* (1977) 136 (suppl): 279–285) disclose the use of albumin to block the solid substrate after the initial coating layer has been applied; Livesey, J. H. et al., *Clin Chim Acta* (1982) 123:193–198 and Hashida, S., et al, *Clin Chim Acta* (1983) 135:163–273 disclose the use of high concentrations of detergent, salt or protein in the sample buffer. These reagents are designed to interfere with nonspecific binding but cannot prevent it completely and cannot quantitate it so as to permit a precise accounting for its effect.

The problem of obtaining false positives is of course, aggravated when the substance to be detected in a biological fluid is present in quite low concentrations, thus necessitating the use of sample which is not greatly diluted. This increases the concentration of potentially interfering materials and thus increases the incidence of false positives. It is recognized by the invention herein, though not generally in the art, that an analogous circumstance arises in normal metabolism in situ at least for vertebrate systems, where specific receptors on target cells must be capable of preferentially binding their specific ligands and rejecting incorrect substances from the surroundings. Other workers have recognized that specific cell-cell adhesion requires a competition between nonspecific repulsion and specific binding (Bell, G. I., et al, *Biophys J* (1984) 45:1051–1064). It has also been demonstrated that cell surfaces in general bear a net negative charge (Mehrishi, J. N. in *Progress in Biophysics and Molecular Biology* (1972), vol 25, Butler, J. A., et al, eds, pp 3–69). It has also been recognized that the anionic surfaces of glomerular basement membrane and of blood vessel walls are responsible, in part, for inhibiting the transport of large anionic serum molecules across them (Seno, S., et al, *Biorheology* (1983) 20:653–662; Brenner, B. M., et al, *Am J Physiol* (1978) 234:5–6).

It has now been found that by mimicking to the appropriate degree (as determined by the method of the invention) the surface repulsion of cell surfaces by the initial layer in solid phase immunoassays, and by balancing the nonspecific binding or "noise" associated with the initial layer on a test portion and control surface portion of a solid support or supports, the specificity of solid phase immunoassay systems can be greatly improved and false positives minimized or eliminated.

DISCLOSURE OF THE INVENTION

The invention provides matrix layers suitable for solid phase immunoassays which are inherently superior in eliminating false positives to those commonly employed. The invention further provides means for verification of the effectiveness of such matrix layers, and for maximizing their effectiveness, as well as for quantitation of background noise.

In one aspect, the invention is directed to solid phase support having a matrix layer which comprises an effective amount of at least one of a component to minimize nonspecific binding (a noise reduction component) and a component to balance nonspecific binding between detecting and control surfaces (noise balancing component). For optimum results, both noise balancing and noise reduction components should be present, but it is, of course, possible to obtain the benefits of one without the other and it may also occur that one material can serve both functions. In another aspect, the invention relates to methods for determining the effective composition of the matrix layer, to detecting target substances in biological fluids using supports coated with this matrix layer, and to methods of preparing these coated supports.

BRIEF DESCRIPTION OF THE DRAWINGS

FIG. 2 shows the titration curve of rabbit antiserum raised against the semen protein p30 using a solid support immunoassay.

FIG. 3 shows the results of a matrix comparison study using an assay for anti-p30 IgG on supports coated with various matrix layer compositions.

FIG. 4 shows the calculated parameters describing the noise reduction and balancing characteristics of various matrix compositions in the tetrads of FIG. 3.

FIG. 8 shows the results of a matrix comparison study to substitute HSA for BSA as noise balancing component.

Figure 1:
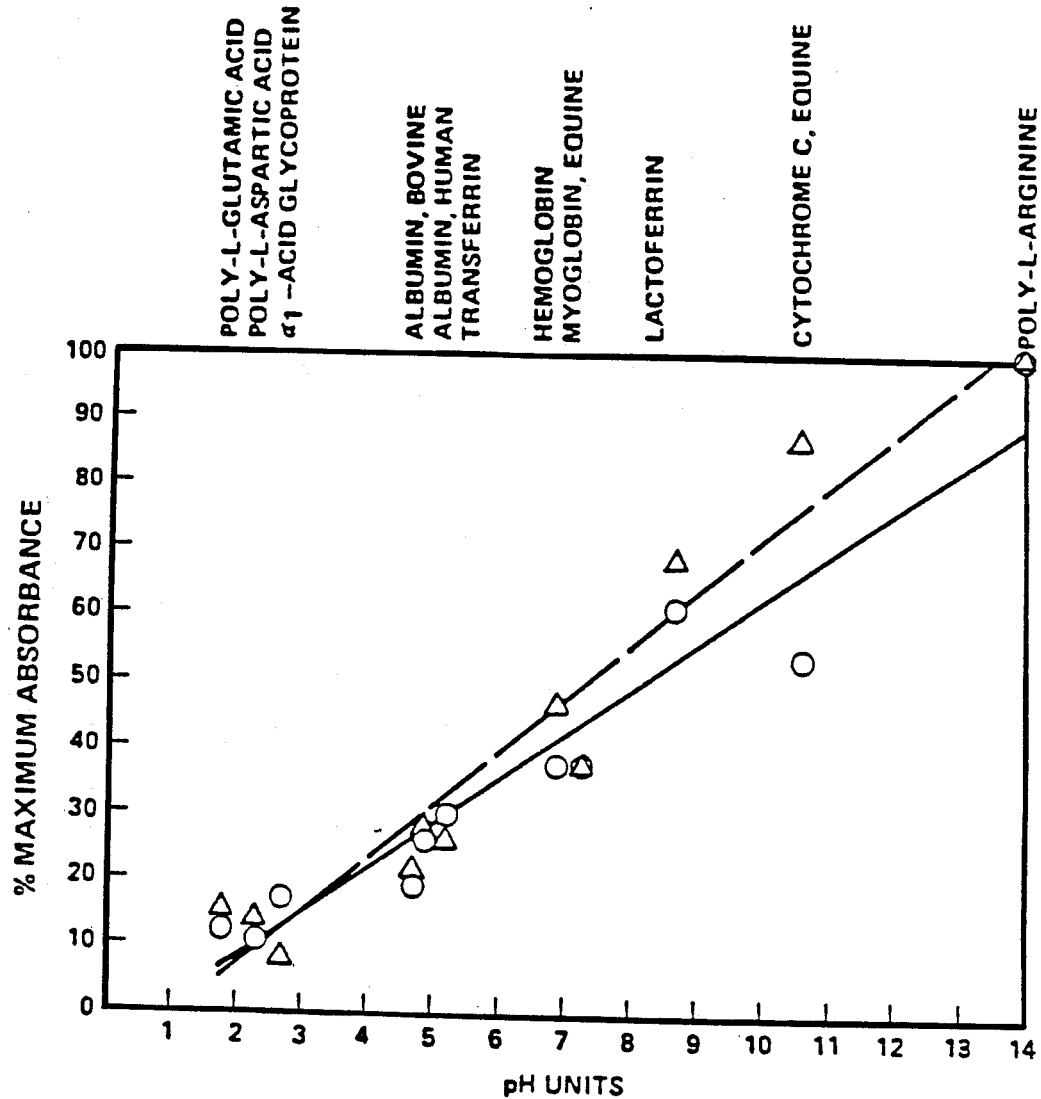
FIG. 1 shows the relationship between binding of a protein (in this case, IgG) to a matrix layer and the isoelectric point of a matrix layer protein component.

MODES OF CARRYING OUT THE INVENTION
SOLID SUPPORT IMMUNOASSAYS

In general, solid support immunoassays depend upon coating a support material, such as a microtiter plate, usually constructed of a hydrophobic material, with an initial layer containing a substance immunospecific for the substance to be detected in the sample, and then in some manner detecting the binding of the material in the test substance. Such immunoassays can be run either by detecting the binding of the target substance, X, itself, or competitively by providing labelled X which can then compete with whatever amount of X may be present in the sample.

In either case, a variety of protocols may be followed. For example, if X is an antibody, the solid surface is coated with a preparation containing an antigen to which the antibody X is specific, the coated matrix is treated with sample, and if X is present it will, of course, bind to the specific antigen and be retained. The presence of X on the solid surface is then determined by a variety of methods, but most usually by treating the solid with a labelled preparation of an "anti-antibody" specific for the species or class of antibody X, and then detecting the presence of label. The label may be fluorescent, enzyme, or radioactivity.

On the other hand, if the substance X to be determined is an antigen, the initial layer will contain an antibody or fragment thereof specific against X; the presence of X in biological samples can then be detected using an additional incubation with labelled antibody or fragment which binds to a different antigenic determinant on X than does the antibody in the initial layer. If the foregoing assays are run competitively, X itself provides the label, and the X in the sample will simply diminish the amount of label bound to the solid. The method and materials of the invention, however, relate primarily to the noncompetitive format or, in general, to "sandwich" assays.

For convenience in discussing the methods and materials of the invention, certain general terms will be applied to the various layers in typical sandwich assays.

The substance whose presence, absence, or amount in a biological sample is to be detected will be referred to as the "target" substance. The target substance can be either antigen or antibody.

The substance specific for the target substance which resides in the initial coating layer on the "solid support" will be referred to as the "surface antitarget". Depending on the nature of the target substance, it will, of course be either an antigen or antibody. The material applied to the other side of the sandwich, which contains a means for detecting the presence of target bound to the solid will be referred to as the "detecting antitarget". While theoretically the detecting antitarget could be an antigen in instances where the target substance is an antibody, most commonly the detecting antitarget is itself an antibody regardless of the nature of the target. If the target substance is an antigen, it will be an antibody which binds to a different antigenic determinant than that of the surface antitarget substance. If the target substance is an antibody, the detecting antitarget is generally an immunoglobulin (Ig) raised against the characteristic species surface markers associated with the target Ig.

In any event, a positive response in the assay comprises a mutilayer composite at the surface of the solid support comprising the surface antitarget, target substance, and detecting antitarget. It should be understood that the detecting antitarget layer can itself comprise a multitude of layers, although this is not generally the case. For example, the detecting antitarget might not itself carry the label, but be bound subsequently to still a fourth layer which does bear such a label.

Because the method of the invention allows noise to be accounted for in a quantitative fashion, it permits assay of low dilutions of biological sample that contain "interferring substances" unrelated to the target which can cause unpredictable noise variations. Such low dilutions are necessary under circumstances where detection of very low level amounts of materials is desired. This is particularly important where target substances are present in very low concentrations, in particular of the order of or less than 100 ng per ml of sample.

A number of materials have normal values at very low levels in serum, and employment of the matrix layer in tests for quantitating these materials is particularly valuable to control noise due to nonspecific binding. Exemplary of such materials are ACTH (15–70 pg/ml); calcitonin (0–28 pg/ml); follicle-stimulating hormone, gastrin-1 (0–200 pg/ml); growth hormone (less than 5 ng/ml); insulin (144 pmol/l); luteinizing hormone, parathyroid hormone (less than 25 pg/ml); prolactin (2–15 ng/ml); renin (less than 10 ng/ml); immunoglobulin E (less than 700 ng/ml). (These estimates of normal values are from the *New Eng J Med* (1986), 314:39–49). Also, sensitive assays for detection are needed for tumor-specific antigens such as carcinoembryonic antigen and p30. Of course, immunodetection of materials from pathogenic microorganisms may require highly sensitive assays since even minimal numbers of such organisms can proliferate and result in disease.

A general problem in control of infectious disease is to diagnose infections when the pathogenic organism cannot be isolated. This is solved in one approach by the use of immunoassays to detect rising antibody titers against the pathogens (*Basic and Clinic Immunology* (1982), Stites, D. P. et al, eds, Lange Medical Publications, Los Altos, Calif., pp 593–636, 672–686). Assays for pathogen-specific antibody which could be improved in specificity and reliability using the method of the invention are those for HTLV/LAV virus (AIDS), hepatitis B virus (serum hepatitis), herpes virus types I and II (herpes encephalitis, and recurrent herpetic ulcers), toxoplasma gondii (congential toxoplasmosis), rubella (congential rubella infection), cytomegalovirus (congenital CMV infection), the various encephalitis viruses, polio virus, and brucella abortus (brucellosis). Because of the ability of the assays of the invention to be conducted at low dilution, in addition to the detection of antibodies, the presence of the limited titers of the antigens related to these disease states per se can also be detected.

It should also be noted that the methods of the invention are applicable to sandwich assays conducted with monoclonal as well as polyclonal antibodies. Indeed, they may be particularly applicable to such assays, since immunoglobulins which are used as components of the matrix layer as the surface antitarget have intermediate isoelectric points and are known to cause nonspecific binding. The increased specificity obtained in assays using monoclonal antibodies rather than polyclonal sera does not alter this nonspecific binding effect which may lead to false positive results.

THE PROBLEM OF FALSE POSITIVES

Ordinarily, the solid phase immunoassays to which the invention applies are conducted by running, in parallel, a "control" portion of the solid support which does not contain the surface antitarget, and a "test" or "detecting" portion of the solid support, which does contain the surface antitarget. Thus, in the "control surface" portion the bottom layer of the sandwich lacks the specific surface antitarget substance. If all worked perfectly, materials which do not contain target would not contain anything to be bound to the solid support in either the control surface or the test region since there is no relevant surface antitarget to hold them. However, to the extent that such binding occurs, it has been assumed that such nonspecific binding could be accurately accounted for simply by subtracting the amount of label nonspecifically bound in the control surface portion from that found in the test portion of the solid support.

As demonstrated herein, this is evidently not true. Even samples which do not contain target substance result in differential binding of the detecting antitarget to the surface antitarget containing (test) and noncontaining (control surface) portions of the support. This is the essence of a false positive. The problem is aggravated at low dilutions of biological test sample, because whatever materials are responsible for the enhanced nonspecific binding in the presence of a surface antitarget are present in larger amounts in these undiluted samples. The noise problem is also aggravated when the surface antitarget has an intermediate charge (e.g., an immunoglobulin) or positive charge.

The matrix layer coating of the invention is capable of damping out this false positive reaction and equalizing the nonspecific binding between the detecting and control surface portions of the solid support. The matrix layer coating may slightly decrease the sensitivity of the test, but effectively eliminates most false positives so that the direct subtracted value (test—control surface) can be used with greater confidence in determining the target substance qualitatively or quantitatively. The direct subtracted value can be computed either by obtaining separate results for signal (test surface) and noise (control surface) and performing the subtraction, or by automated reference well subtraction using analog methods in the circuitry of a detector.

MATERIALS IN THE MATRIX LAYER

Two types of materials are generally required for the most effective matrix layer. The number of materials actually used to contruct the matrix layer may be more or less, depending on the circumstances of the assay, as will be explained below.

One component (or components) serves to decrease nonspecific binding by providing a generally repulsive surface mimicking that ordinarily found on the surface of cells. This component will be referred to as the "noise reduction" component since it reduces nonspecific binding of all kinds, not only that which leads directly to false positives by being unbalanced in favor of layers containing surface antitarget. In general, the noise reduction component will provide an anionic barrier and will be, therefore, a negatively charged material, preferably a macromolecule. Certain proteins, for example, are known to be highly negatively charged at neutral pH; for example, human α-1 acid glycoprotein (AGP), having a pI of 2.7, is an effective choice.

The other component (or components) of the matrix layer of the invention is designated a "noise balancing" component. This component is selected for its ability to balance the nonspecific binding of known negative samples between the detecting and control surface wells. Bovine serum albumin (BSA) or human serum albumin (HSA) appear to be effective choices for the noise balancing component of the matrix.

Other components may also be included in the matrix of the invention, but the foregoing components are required. It should be noted, however, that the same material may in some cases be effective both as a noise balancing and noise reduction component; in addition, the noise balancing component may be a conventional part of the assay, such as the use of immune and nonimmune serum in assays for a target antigen wherein the serum components may balance noise.

The proteins suggested above for the noise reduction and noise balancing components of the matrix system are of course merely illustrative, and other proteins, or other macromolecular substances capable of binding to the usually hydrophobic support either covalently or noncovalently, or mixtures of such materials, could also be used. As a noise reduction component, any negatively charged (at neutral pH) protein, glycoprotein, polyamino acid or other natural or synthetic macromolecule could be used.

Exemplary of the polyamino acids are poly-L-glutamic acid and poly-L-aspartic acid. Exemplary of other macromolecules are proteins such as albumins or α-globulins, glycoproteins such as α-acid-glycoprotein, mucins, fetuin, or red cell glycophorin; exemplary polysaccharides and proteoglycans include heparin, hyaluronate, chondroitin sulfate, keratan sulfate, and dermatan sulfate; exemplary glycolipids include gangliosides; and other macromolecules include cross-linked dextran and agarose gels substituted with carboxymethyl or sulfopropyl groups, and detergents with large branching anionic hydrophilic head groups. A variety of macromolecules could be designed. In general, their characteristics include a hydrophilic anionic region, a sufficient hydrophobic region to provide nonspecific binding to the solid support or, in the alternative, to provide linking groups for the purpose of effecting covalent bonding to the support. Substances of great complexity may not, in fact, usually be necessary for the noise reducing component as is evident from the illustration below. However, they may turn out to be optimal components in some assays for a specific target substance. Because only small quantities of the noise reducing components are required and because prospective components can be easily screened by the methods described herein, even expensively designed components would not greatly add to the cost of the assay.

With respect to the noise-balancing component, again, any properly designed synthetic macromolecule or a variety of naturally occurring macromolecules could be used. In general, the noise-balancing components contain both regions of hydrophobic character and of hydrophilic character, and the steric characteristics should be such that blockage of binding through steric interaction is also possible. Suitable exemplary materials include bovine serum albumin and human serum albumin, used successfully in the illustration below, serum α-globulins and α-lipoproteins, as well as synthetic peptides which contain both hydrophilic and hydrophobic regions. As is the case with the noise reduction component, the amount of material required to provide an effective matrix layer is sufficiently small that even costly materials can economically be used.

In instances where the target substance is an antigen, immune and nonimmune sera from the same species may be included in the surface layer, and the surface antitarget is then the antibody in the immune serum. The remaining components of the immune and nonimmune serum constitute the noise balancing component of the matrix since these materials may be close to identical in both control surface and test portions. To complete the matrix layer in this case, only the addition of an anionic charged protein or other macromolecule to provide the noise reduction component may be needed. On the other hand, in some instances it may be difficult to obtain non-immune serum which contains the same collection of interferring substances as does the immune serum. In any event, the method of the invention defines a noise balancing parameter that (HG) may be used to verify this noise-balancing capacity of the non-immune serum.

The solid support to which the matrix is applied may include any convenient surface, usually, but not necessarily, hydrophobic, most commonly a microtiter plate, but including also plastic tubes, plastic balls, magnetic balls or gels, paper discs, and cellulose-like beads or gels. The binding of the matrix to the substrate can be by a variety of techniques which include passive adsorption based on hydrophobic bonding, charge binding or other methods of nonchemical binding as well as covalent linkage of the matrix layer either directly or by use of an intermediary substance coated to the support.

The surface antitarget is most conveniently added to the matrix components prior to coating the initial layer on the support. A two-step coating procedure may also be used. For example, the surface antitarget can first be added to the test portions of the surface, in concentrations sufficiently low that the surface is only partly coated, followed by coating or binding with matrix layer or the reverse. Indeed, the supports might be supplied already coated with matrix layer and the specific surface antitarget added according to the specific assay to be employed. This might require that the surface antitarget to be added by means other than simple coating, such as accelerated ion implantation or electrophoresis.

It should be noted that either noise reduction or noise balancing component can be used alone if desired. In this regard, proteins used in the art for blocking nonspecific binding, such as BSA, are generally used in concentrations of 5–30 mg/ml—or about 1000 fold the effective concentrations in the matrix layer. As is clear from the results of the assays set forth in Examples 2 and 3 below, use of BSA as a block is not effective in balancing noise.

METHOD TO OPTIMIZE AND VERIFY MATRIX LAYER COMPOSITION

The invention further offers a method to verify on an ongoing basis the effectiveness of the particular matrix layer chosen, as well as to select optimal components for the matrix initially, through an analytical system designed to maintain assay sensitivity while achieving noise reduction and noise balance. A straightforward analysis to evaluate various matrix compositions can be used to generate a parameter designated a "matrix index", which is defined as the product of a sensitivity ratio (SR), a signal to noise ratio, ((S/N)R), and a noise balance ratio (NBR). While the direct product of these parameters serves as an arbitrary index, as in the explanation below, it may be desirable to weigh, for example, noise balance ratio more heavily than the other parameters in computing an appropriate matrix index. However, the matrix index which is calculated as $SR \times (S/N)R \times NBR$ serves at least as a convenient screening parameter.

The invention herein includes a particularly preferred and convenient method of designing a protocol to determine simultaneously the values of all three parameters which collectively influence the matrix index. However, a wide variety of experimental designs is possible, and each parameter could be determined independently. The sensitivity ratio could be determined simply by running the assay with and without a particular matrix layer composition; the noise balance ratio can be determined by comparing the behavior of samples not containing target in the presence or absence of surface antitarget, and the signal-to-noise ratio can be determined by comparing the binding of samples with and without target to matrix layers containing surface antitarget. A wide variety of experimental designs is possible, and will vary with the number of components intended to be included in the matrix. The illustration below is for the typical case, where one component is being tested as a noise reduction component and another as a noise-balancing component. This assay design is merely illustrative, and does not limit the scope of approaches and experimental protocols which determine fundamentally the same parameters making up the matrix index.

In this preferred and illustrative embodiment, the values of the parameters which make up the matrix index can be determined independently and conveniently by analysis of a series of tetrads which contain either no matrix layer or various test matrix formulations. Each tetrad contains portions with and without surface antitarget and with and without application of a target substance. The tetrads form a pattern as shown below:

| | target | no target |
|---|---|---|
| surface antitarget | A | C |
| no surface antitarget | B | D |

Of course, this particular pattern is arbitrary and any configuration which contains these elements may be used. In the discussion below, "wells" is used to refer to any defined portion of the support surface. Such portions can be defined, for example, as fractions of collections of beads or particles, areas in a column, or, in the conveniently used microtiter plates, actually as wells.

Referring to the configuration shown above, wells A and C contain surface antitarget; wells B and D do not. Wells A and B will be supplied target substance, wells C and D will not.

It will be recognized that the pairs of wells (A and B) and (C and D) each comprise the usual test and control surface wells as such assays are ordinarily conducted. Wells C and D will also serve to illustrate that in the absence of matrix layer, or in the presence of inappropriately constructed matrix, nonspecific binding of detecting antitarget for samples containing no target substance may be differential in the presence or absence of surface antitarget. By comparing a series of tetrads with various matrices, those matrices which produce identical readings in wells C and D clearly balance the noise due to nonspecific binding; those which produce least response in C as compared to A reduce the noise level relative to the best, and those which provide the highest corrected reading for A (after B is subtracted) show the greatest sensitivity.

In this particular protocol, the noise balance ratio, NBR, is defined as the ratio of the signals in C and D, with the smaller of the two values placed in the numerator. NBR is thus C/D or D/C.

In this protocol, the signal to noise ratio, (S/N)R, is defined as the corrected signal (A-B) divided by C. The noise is the apparent signal produced in the presence of surface antitarget but in the absence of target in the sample. C is used rather than B in the denominator because, in order to evaluate noise, higher concentrations of nontarget substances in the sample (e.g., as found in serum or other biological test samples) often are used in C and D than are provided in A and B. In other words, a relatively high sample dilution (containing target) may be used for A and B but a relatively low one (without target) for C and D.

In this protocol, the sensitivity ratio, SR, is not a parameter associated with each tetrad per se but rather the ratio of the corrected signal in a test tetrad as compared to that in a tetrad containing no matrix. This provides a measure of the loss of sensitivity due to the presence of the matrix layer. SR represents the ratio of the difference A-B in the matrix coated tetrad divided by the difference A-B for the tetrad not coated with matrix.

In order properly to evaluate these parameters, the surface antitarget, target substance, and matrix providing materials should be provided at dilutions or concentrations in accordance with certain optimization considerations. In general, for immunoassays which employ passive adsorption to polystyrene microtiter wells, for example, the surface antitarget should be applied at a concentration of less than 10 μg/ml as higher concentrations may lead to decreases in assay sensitivity due to the "hook" effect. In fact, concentrations less than 1 μg/ml are convenient. The target substance is supplied at a concentration which is in the linear region of its titration curve against the selected concentration of surface antitarget. The linear region may be determined by titrating serial dilutions of biological sample containing target substance against the surface antitarget. The linear region is selected because interference caused by the matrix layer to surface antitarget binding to target will be detected immediately by a linear loss of assay sensitivity. The dilution of a corresponding background sample of biological fluid containing no target is optimally a low dilution (about 1:1-1:9, v/v) in order to enhance the noise level for evaluation. A titration curve for the background fluid against the selected concentration of surface antitarget may also be determined.

Matrices of various compositions are tested using a series of test tetrads. Each tetrad represents a unique formulation of matrix components. Each tetrad is evaluated internally for noise reduction and balance, and relative to a tetrad containing no matrix for sensitivity. An arbitrarily determined product of these factors, the matrix index, then gives a measure of the effectiveness of the matrix layer for each tetrad in optimizing the assay. The matrix layer composition having a noise balance ratio close to unity and the highest matrix index, or, if desired, an alternatively weighted product of the above parameters, is chosen.

The validity of the noise-balancing aspect of the matrix layer composition is verified during the conduct of a typical assay. In a typical assay, one or more negative samples having intermediate to high background noise levels can be tested in both the detecting and control wells. The binding of these samples should be essentially equal in both wells, yielding a noise-corrected signal close or equal to zero. This confirms that the noise balance feature is properly adjusted for that day's run. Standard positive controls will also be run each day to confirm that the surface antitarget-containing detecting wells are also properly adjusted.

If desired, samples identified as positive during testing may be verified by a competition assay. An appropriate dilution of the positive sample (sufficiently diluted to yield a weak but statistically significant positive) can be preincubated with a soluble form of the surface antitarget substance (generally in a concentration range ≦25-50 times the concentration of antitarget used to coat the test surface). This preincubation with soluble antitarget will competitively inhibit binding of the target to the test surface. Hence, binding of these preincubated samples should be essentially equal in both detecting and control wells, again yielding a noise-corrected signal close or equal to zero. Thus, the ability of the matrix layer to balance nonspecific binding (noise) between the detecting and control wells, and its ability effectively to eliminate most false positives can be verified on an ongoing basis by including proper negative and (if desired) positive controls for each assay run.

EXAMPLE

The following examples are intended to illustrate but not to limit the invention.

PREPARATION A

Preliminary Screening of Coating Components

Initial selection of suitable matrix components which reduce noise by inhibiting nonspecific binding of rabbit IgG and of rabbit nonimmune serum was determined by comparison to test surfaces coated with poly-L-arginine, a positively charged polymer.

Immulon II Removawells (Dynatech Laboratories, Alexandria, VA) were coated overnight at 4° C. with 10 μg/ml of the components to be tested in coating buffer (0.1 M sodium bicarbonate, pH 9.8) (0.35 ml/well), the wells were washed and detergent blocked with 0.4 ml/well of phosphate buffered saline containing 0.05% Tween-20 ("PBS-T", which is 0.15 M NaCl, 0.01 M phosphate, pH 7.4, 0.05% Tween-20).

The wells were incubated at room temperature for 90 minutes with 0.35 ml/well antigen buffer (PBS-T with 10 mM EDTA) containing either 0.5 mg/ml pooled rabbit IgG or a 1:4 (v/v) dilution of reconstituted pooled rabbit serum (both nonimmune, hence representing sample background noise). After washing with PBS-T, the bound serum immunoglobulins or antibodies were detected by incubating for one hour at room temperature with goat anti-rabbit IgG labelled with alkaline phosphatase (Sigma Chemical Co., St Louis, MO) at 1:1499 (v/v) dilution in PBS-T, followed by treating with 4 mM p-nitrophenyl phosphate in substrate buffer (10% diethanolamine, 0.01% magnesium chloride, 0.02% sodium azide, pH 9.8) for 30 minutes at 37° C. The enzymatic reaction was stopped with 50 μl of 4 M sodium hydroxide and the absorbance was read at 410 nm on a MICROELISA minireader (Dynatech Laboratories, Alexandria, VA).

In all cases a % maximum absorbance was obtained using the poly-L-arginine coat set arbitrarily at 100% maximum. The series consisted of proteins, glycoproteins, and synthetic polypeptides of differing isoelectric points. A progressively increasing percentage of the maximum absorbance was observed, in direct correlation with the increasing isoelectric points of the proteins. The correlation was substantially linear, as shown in FIG. 1.

In FIG. 1, the precent maximum absorbance for binding of IgG from pooled rabbit IgG and rabbit serum as measured by ELISA is plotted against the isoelectric point of each coating peptide. The average absorbance for binding of rabbit IgG from the pooled IgG ($A_{410} = 1.76$) and pooled serum ($A_{410} = 1.23$) to the poly-L-arginine coat by ELISA was set as 100% of maximum absorbance respectively. The % maximum absorbance for (IgG binding to) protein X (in the test well coat) is thus calculated relative to these values. Separate regression lines for % maximum absorbance representing binding of IgG from pooled rabbit IgG and pooled rabbit serum were calculated by least squares. Each point is the average of duplicate determinations in a single experiment.

The isoelectric point of the coating peptides and glycopeptides are as follows:

| | | |
|---|---|---|
| Poly-L-glutamic acid | 1.8 | |
| Poly-L-aspartic acid | 2.3 | |
| $\alpha_1$-acid glycoprotein, human[1] | 2.7 | |
| Albumin, bovine serum[2] | 4.7 | |
| Albumin, human serum[1] | 4.9 | |
| Transferrin, human[1] | 5.2 | |
| Hemoglobin, human[3] | 6.9 | |
| Myoglobin, equine[4] | 7.3 | |
| Lactoferrin, human breast milk[1] | 8.7 | |
| Cytochrome c, equine heart[1] | 10.6 | |
| Poly-L-arginine | 14.0 | |

Estimated isoelectric points for the synthetic polypeptides were calculated from the Henderson-Hasselbach equation using approximate $pI_a$ values of the ionizable side chain groups. The number of amino acid residues were calculated from the estimated molecular weights: poly-L-glutamic acid ($M_r = 60,000$); poly-L-aspartic acid ($M_r = 20,000$); and poly-L-arginine ($M_r = 100,000$). By Henderson-Hasselbach analysis, poly-L-arginine would still have an overall positive charge as the pH approached 14. Hence, this theoretical pH was designated as its isoelectric point for purposes of this analysis. The isoelectric point for lactoferrin represents an average for the reported range of 8.2–9.2.

The remaining pI values were obtained from the literature as follows:
1. Fasman, G.D., ed, *Handbook of Biochemistry and Molecular Biology* (1975), vol II, CRC Press, Cleveland, OH.
2. Malamud, D., et al, *Anal Biochem* (1978) 86:620–624.
3. Righetti, P.G., et al, *J Chromatog* (1976), 127:1–28.
4. BDH Chemicals Ltd. *Isoelectric Point Markers, Product Information*, pp 1–5, Poole, England.

This suggests that the nonspecific binding of IgG alone or in serum to a hydrophilic protein-coated surface is primarily a function of the surface charge imparted by the coating protein. Nonspecific hydrophobic binding in these assay systems is inhibited by inclusion of detergents in the test sample buffers. From these results one would also expect that those substances with the lowest percentage of maximum absorbance (i.e., those with the lowest isoelectric points) would be substances most likely to serve as effective noise reduction components in a matrix.

Figure 5A:
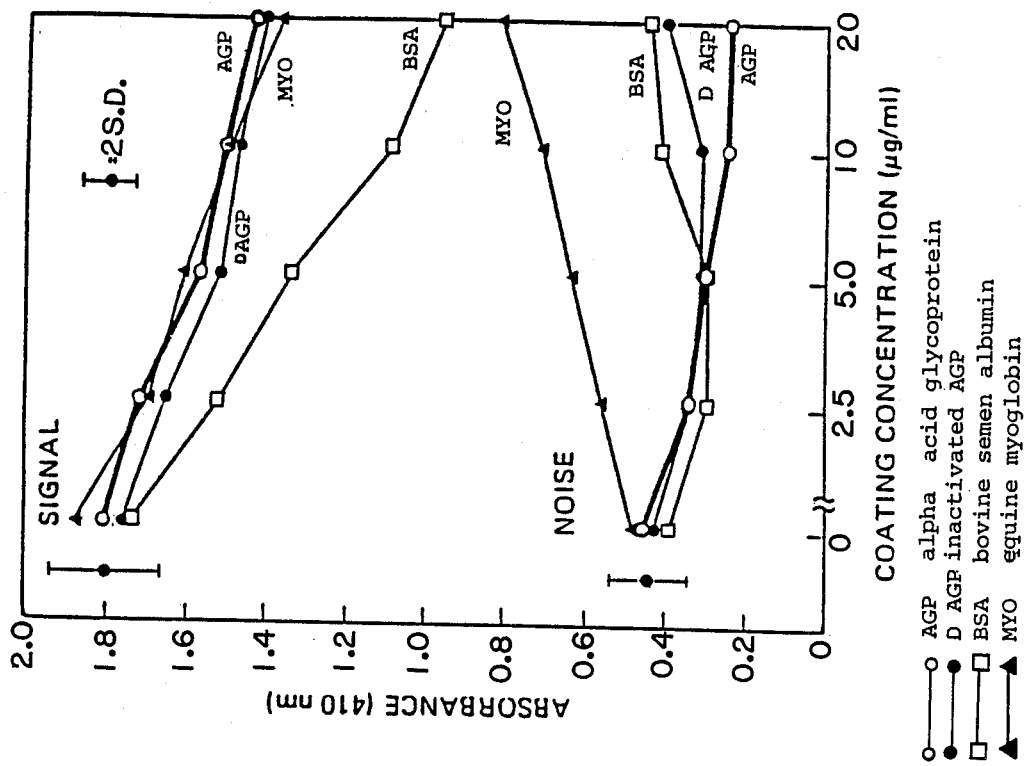
FIGS. 5A and 5B show the results of coating solid supports with matrix layers comprised of various proteins on sensitivity, noise, and signal-to-noise ratio.
Figure 5B:
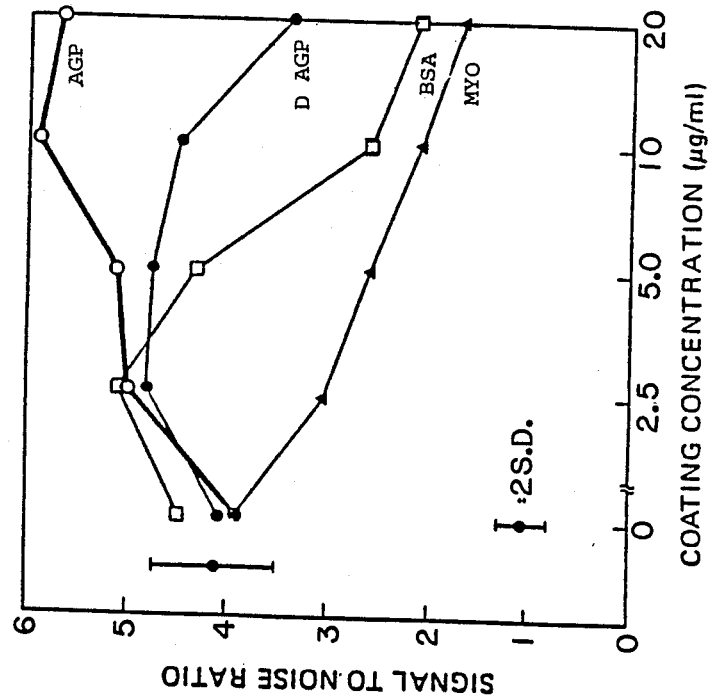

To further test the ability of proteins of differing isoelectric points to decrease assay noise, several of the proteins tested in the foregoing protocol were coated at various concentrations to test their effects on the signal to noise ratio in an ELISA conducted generally as described in Example 1 below. The results of this assay are shown in FIG. 5A; all proteins consistently decreased the signal, but proteins having a net negative charge also decreased noise at low concentration. As shown in FIG. 5B, the signal to noise ratio improves initially with small amounts of all negatively charged proteins, and maintains an improvement to a high concentration for AGP (the most negatively charged). Thus, AGP appears to be the best candidate in this series of test substances for use as the noise-reducing component in a matrix. Desialization of the AGP using standard procedures depletes it of negative charge and significantly diminishes its ability to maintain a high signal to noise ratio.

EXAMPLE 1

Optimization of Matrix Coat

An optimized matrix was determined for a particular application in the assay of biological samples for anti-p30 antibody. The antigen p30 is a 30kd glycoprotein which is found in human semen and appears to be generated only in males. An assay for the antigen using a sandwich approach on solid supports without the matrices of the invention, was disclosed in Graves, H.C.B. et al. *New England Journal of Medicine* (1985) 312:338–343.

Because p30 appeared to be male-specific, it was reasoned that some sexually active women might become sensitized to this foreign substance and make antibodies to it. Such antibodies, if found, could contribute to problems with fertility or vaginitis in these women. To investigate this possibility, an optimized matrix coat for assay noise control was designed for an immunoassay to detect low levels of anti-p30 antibody. In the determination herein, the target substance is anti-p30 IgG in rabbit serum, the surface antitarget is p30 protein (purified as described by Sensabaugh, G.F. *J Forensic Science* (1978) 23:106–115), and the detecting antitarget is alkaline phosphatase-labeled goat antibodies specific for rabbit IgG.

To design an optimized matrix coat, Immulon II ™ flat bottom Removawells (Dynatech Laboratories, Alexandria, VA) were divided into tetrads of the general pattern described hereinabove, each tetrad containing two test and two blank control wells. The blank control wells, B and D of each tetrad, were coated with test matrices containing various concentrations (0–10 μg/ml) of the noise reduction component, human alpha-1 acid glycoprotein (AGP) and various concentrations (0–8 μg/ml) of the noise balancing component, bovine serum albumin (BSA), RIA grade. (Both substance were provided by Sigma Chemical Co., St. Louis, Mo.) The test wells, A and C of each tetrad were coated with the corresponding matrices containing 1 μg/ml of purified p30 antigen (surface antitarget). Coating was carried out in "coating buffer" (0.1 M bicarbonate, pH 9.8) at 4° overnight.

The coated plates with the tetrads containing blank control and test wells were washed three times, 0.40 ml/well, with PBS-T (see Preparation A). The plates were then blocked using 0.4 ml/well PBS-T for 1 hour at room temperature.

The coated, washed, blocked, plates were then used to assay for the presence or absence of target substance, rabbit antibody to p30, by incubating wells A and B of each tetrad with a 1:999 (v/v) dilution of pooled polyclonal antiserum (raised in rabbits against purified p30 antigen) in antigen buffer (0.05 M HEPES, pH 7.4, 0.4 M NaCl, 10mM EDTA, 0.05% Tween-20) for 1½ hours, at 0.35 ml/well, at room temperature. (This dilution had been determined by titrating the rabbit antiserum using wells coated as above, without matrix components, but with 1μg/ml purified p30 antigen, and detecting the bound antisera using alkaline phosphatase labelled goat anti-rabbit IgG as described below. The results of this titration, shown in FIG. 2, indicate that a 1:999 (v/v) dilution is in the linear portion of the curve.

Wells C and D of each tetrad were correspondingly incubated with a 1:4 (v/v) dilution in antigen buffer of nonimmune serum obtained from rabbits of the same species which had not been subjected to immunization with p30.

The plates were again washed four times with 0.4 ml/well PBS-T and the bound antibody was detected by incubating all wells for one hour at room temperature with 0.35 ml/well of a 1:1499 (v/v) dilution of detecting antitarget, goat anti-rabbit IgG labelled with alkaline phosphatase (Sigma Chemical Co., St. Louis, MO).

The plates were then washed three times with 0.40 ml/well PBS-T and incubated at 37° C. with 0.25 ml/well of substrate solution containing 4 mM p-nitrophenyl phosphate in substrate buffer (10% diethanolamine, 0.01% magnesium chloride, 0.02% sodium azide, pH 9.8). The enzyme reactions were stopped with 4 M NAOH, 0.05 ml/well, after 30 minutes, and the absorbance of each well read at 410 nm on a MICROELISA reader (Dynatech Labs, Alexandria, VA).

The results, given in corrected absorbance units at 410 nm, for a plate of 9 tetrads is shown in FIG. 3. Blank control wells which were treated with nonimmune serum diluted 1:4 (v/v) but not with detecting antitarget were arbitrarily set at 0 to obtain a corrected reading for wells A, B, C, and D.

Using the formulas set forth above, a sensitivity ratio, signal to noise ratio, and noise balance ratio were calculated for each tetrad representing a different matrix formulation, and a matrix index for each obtained. The wells are designated by their horizontal (matrix concentration of BSA) and vertical coordinates (matrix concentration of AGP) in FIG. 3.

Of course, the SR for well 0.0 is 1 by definition; the SR for well 0.5 is 1.72/2.0 or 0.86; that for well 0.10 is 1.69/2.0 or 0.85, and so forth.

The (S/N)R for each well is calculated independently as $(A-B)/C$ (i.e. the reading obtained for A minus B (zero in this case) divided by the signal for C which represents the noise due to nonspecific binding of nonimmune serum at low dilution). Thus, for well 0.0 (S/N)R is 2.0/0.39 or 5.1; for well 0.5 (S/N)R is 1.72/0.23 or 7.5; for well 0.10 it is 1.69/0.17 or 9.9, and so forth.

This series of wells represents increasing concentrations of noise reduction component in the matrix. It is clear that the signal to noise ratio is desirably affected. Corresponding values of the signal to noise ratios for wells 4.0 and 8.0, which contain increasing concentrations of noise balancing component of the matrix are 6.2 and 4.9 respectively. It is apparent that this component is not very helpful with respect to signal to noise ratio reduction, and has an undesired effect at concentrations of 8 $\mu$g/ml or greater.

The noise balance ratio (NBR) is calculated as the ratio of C/D or the reciprocal, depending on which is greater, and is ideally one, where noise is perfectly balanced. For proper assay noise control, it is essential that the NBR be as close to one as possible, as this allows one to measure the "noise" of the test sample in the blank control well and subtract it from the test well signal. In the control tetrad 0.0 the NBR is 0.39/0.16 or 0.41; for increasing amounts of the noise reduction component this ratio improves but does not approach one; in tetrad 0.5, the NBR is 0.48; in tetrad 0.10 it is 0.71. However, marked improvement is found as increasing amounts of the noise balancing BSA component are added. In tetrad 4.0 the NBR is 0.92; in tetrad 8.0, it is 0.68, indicating that an excess of this component has overbalanced the noise.

FIG. 4 shows a summary for the results for all 9 tetrads; listed in order are SR, (S/N)R, NBR, and finally, MI (the matrix index).

FIG. 4 shows that the optimum matrix composition in this series is represented by tetrad 4.10. This matrix seems to achieve the proper balance of noise reduction component and noise balancing component. The sensitivity of the assay is diminished only slightly; indeed roughly the same order of diminution in sensitivity is found in all tetrads containing matrix. The higher matrix index for tetrad 4.10 than for 4.0 appears to be due mainly to an enhancement of the signal to noise ratio, as well as some improvement in balance, as would be expected from the increased concentration of the noise reduction component (AGP) of the matrix. Note that the lowest matrix index (i.e., the tetrad with the poorest noise control) was obtained for tetrad 0.0 which contained no matrix coat. This is the standard configuration for current solid phase immunoassays.

EXAMPLE 2

The Use of the Matrix in Noise Detection Elimination of False Positives

Comparative analyses with and without the matrix coating on the solid support were conducted using anti-p30 rabbit serum, nonimmune rabbit serum, purified nonimmune rabbit IgG and poly-L-lysine, a prototype for a cationic cross-reacting substance. The assays were conducted precisely as set forth in Example 1, but with the blocking step either conducted as above with (PBS-T) or with a PBS-T containing 1% BSA (wt/v). The matrix coat is 10 $\mu$g/ml AGP+4 $\mu$g/ml BSA and the surface anti-target in the test wells is p30 at 1 $\mu$g/ml. The matrix thus corresponds to tetrad 4.10 of Example 1. The results are shown in Table 1 below.

TABLE 1

|  |  | *IS 1:999 | NS 1:4 | NS 1:1 | IgG 1 mg/ml | poly-L 10 μg/ml |
|---|---|---|---|---|---|---|
| No matrix (Block: PBS-T) | Test | 1.50 | .32 | .53 | .49 | 1.07 |
|  | Ctrl Sfc | .00 | .23 | .36 | .14 | .22 |
|  | Corrected | 1.50 | .09 | .17 | .35 | .85 |
| No matrix (Block: BSA 1% in PBS-T) | Test | 1.87 | .60 | .86 | .74 | 1.16 |
|  | Ctrl Sfc | .00 | .18 | .35 | .12 | .54 |
|  | Corrected | 1.87 | .42 | .51 | .62 | .62 |
| Matrix Coat (Block; PBS-T) | Test | 1.29 | .20 | .27 | .32 | 1.51 |
|  | Ctrl Sfc | .00 | .20 | .29 | .28 | 1.66 |
|  | Corrected | 1.29 | 0 | −.02 | .04 | −.15 |

*IS = rabbit antiserum pooled from rabbits immunized against p30;
NS = pooled rabbit nonimmune serum;
IgG = purified nonimmune rabbit IgG from a different pool;
poly-L = poly-L-lysine.

The results are clear that whether blocking was conducted with Tween (PBS-T) alone or Tween plus BSA, all known negatives gave false positive results. This was true even though the control surface well reading was subtracted from the test well reading. However, when the matrix coat was used, neither the nonimmune serum nor IgG controls gave noticeable positive readings; the result for poly-L-lysine was greatly improved, though less than perfectly balanced. Cationic poly-L-lysine is electrostatically attracted to the negatively charged matrix.

EXAMPLE 3

Assay of Human Serum for anti-p30 with Matrix Coat Control

The method of Example 2 was applied generally as there described except that the detecting antibody was alkaline phosphatase labelled goat anti-human IgG F(ab')2 specific for the gamma chain of human IgG (Sigma Chemical Company, St. Louis, MO).

Human sera from 19 men and women were tested with and without matrix coat control, wherein the matrix coat is obtained by incubating the Immulon II ™ Removawells in 10 μg/ml human AGP and 4 μg/ml BSA in coating buffer; for the the detecting wells the matrix composition is in admixture with 1 μg/ml p30. For the standard ELISA (used here for comparison), p30 at 1 μg/ml in coating buffer was used for the detecting wells, and coating buffer alone for the blank control wells.

After coating overnight at 4° C., the support was washed as above and blocked either with PBS-T or PBS-T with 1% BSA, by incubating for one hour at room temperature. The supports were again washed as above, prior to the application of sample. Human sera were supplied as a 1:2 dilution (v/v) in BSA-antigen buffer (0.05 M HEPES, pH 7.4, 0.6 M NaCl, 15 mM EDTA, 0.75% v/v Tween-20, 1.5% wt/v RIA grade BSA), after a one-half hour incubation in test tubes. Incubation in the wells was for 1.5 hours at room temperature. The supports were again washed, and bound target detected as described in Example 2, but with the above-mentioned appropriate detecting antitarget. The results are shown in Table 2 and are plotted in FIG. 6.

TABLE 2

ELISA to Detect Human IgG Antibody Specific for p30: Comparison of Matrix Coat Control with Tween-20 and BSA-Tween-20 Coat Control

| Subject | A | B | C | D | E | F | G | H | I | J | K | L | M | N | O | P | Q | R | S |
|---|---|---|---|---|---|---|---|---|---|---|---|---|---|---|---|---|---|---|---|
| ELISA with Matrix Coat Control |
| Detecting Well | .12 | .27 | .16 | .22 | .15 | .55 | .53 | .39 | .42 | .33 | .15 | .19 | .38 | .14 | .10 | .19 | .22 | .18 | .23 |
| Control Well | .08 | .25 | .13 | .21 | .15 | .12 | .19 | .42 | .42 | .26 | .11 | .19 | .35 | .11 | .11 | .20 | .23 | .22 | .25 |
| Corrected Signal | .04 | .02 | .03 | .01 | 0 | .43 | .34 | −.03 | 0 | .07 | .04 | 0 | .03 | .03 | −.01 | −.01 | −.01 | −.04 | −.02 |
| ELISA with Tween (0.05%) Block |
| Detecting Well | .35 | .39 | .55 | .60 | .35 | 1.00 | 1.60 | .80 | .74 | .62 | 1.10 | .51 | .55 | .65 | .35 | .65 | .56 | .53 | .92 |
| Control Well | .31 | .54 | .36 | .50 | .36 | .39 | .55 | .89 | .83 | .53 | .44 | .45 | .67 | .36 | .44 | .72 | .79 | .69 | .59 |
| Corrected Signal | .04 | −.15 | .19 | .10 | −.01 | .61 | 1.05 | −.09 | −.09 | .09 | .66 | .06 | −.12 | .29 | −.09 | −.07 | −.23 | −.16 | .33 |
| ELISA with BSA (1%) and TWEEN (0.05%) Block |
| Detecting Well | .40 | .61 | .48 | .60 | .36 | 1.19 | 1.75 | 1.00 | .85 | .81 | 1.00 | .49 | .59 | .70 | .35 | .60 | .51 | .48 | .95 |
| Control Well | .32 | .59 | .30 | .53 | .32 | .37 | .67 | 1.08 | .90 | .70 | .45 | .45 | .66 | .32 | .47 | .77 | .74 | .63 | .43 |
| Corrected Signal | .08 | .02 | .18 | .07 | .04 | .82 | 1.08 | −.08 | −.05 | .11 | .55 | .04 | −.07 | .38 | −.12 | −.17 | −.23 | −.15 | .52 |

Figure 6:
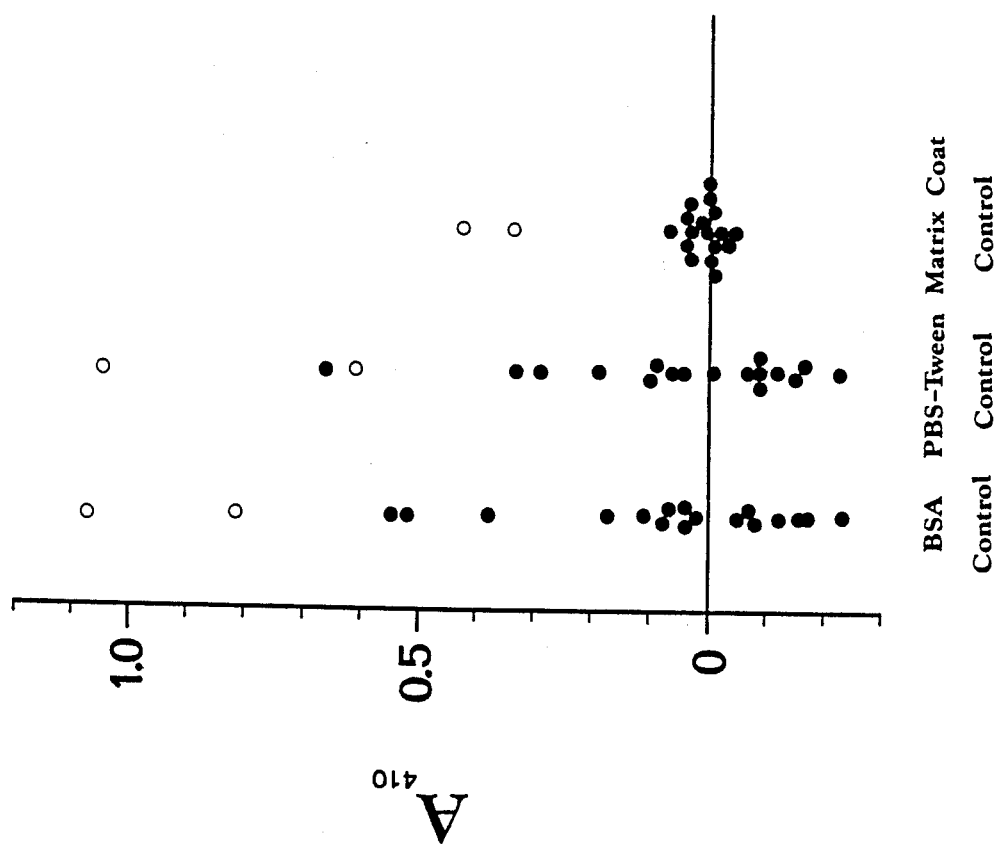
FIG. 6 shows the results of ELISA determination of anti-p30 IgG in human serum samples with and without matrix coat noise control.

It is apparent from the examination of FIG. 6 that matrix coat controlled assay samples showed clear positive or negative results, whereas the assays run in the absence of matrix gave a considerable spread, which depending upon its interpretation, includes false positives. In particular, subjects K, N, and S had elevated signal levels using ELISA without matrix control, although matrix coat control showed them to be negative for anti-p30. Samples F and G, which were positive in the matrix controlled assay, were shown to actually contain anti-p30. By preincubating 1:4 (v/v) dilutions of these samples with 50 μg/ml of purified p30, signals in these samples dropped to nonimmune background levels, i.e., approximately zero.

Also of importance, these results demonstrate that the "noise level" measured for each individual test sample was unique to that sample. To determine the magnitude of target-specific signal present in a sample, one must be able to measure the amount of noise present in the sample. This must be done in a noise-balanced assay, i.e., the subtracted noise cannot be altered by the presence or absence of antitarget on the control surface. For example, subjects H, J, and M had relatively high signal levels in the detecting wells containing the matrix coat with p30, but they also had essentially identical signal levels in the blank control wells which contained only the matrix coat. This indicates that the detecting well signal was not specific for the antitarget (i.e., p30).

Because the noise level in general is unique to each sample (as demonstrated here), correct assay results depend upon the ability to measure this noise accurately so that it can be subtracted from the detecting well signal. Because the control surface well is made an accurate measure of noise by the method of the invention, this subtraction becomes feasible, thereby providing a valid measure of signal. Also note that matrix coat noise control tightly clusters negative sample values around zero (i.e, decreases variance) a feature that dramatically simplifies the statistical calculations necessary for data analysis.

EXAMPLE 4

Detection of Anti-BSA in Humans

Nine of 10 samples of human sera tested as described below, using a matrix coat control wherein HSA was substituted for the surface antitarget BSA in the control wells, showed the presence of antibodies to BSA. The presence of this antibody in the population may account for a measurable portion of nonspecific binding in solid phase assays run on human samples if BSA is used in a blocking step of the assay. Therefore, as this assay demonstrates, false positives may also be minimized by pretreating the samples to be tested with an effective amount of BSA in the antigen buffer.

For this assay, both control and test wells were incubated with 1 μg/ml human serum albumin (HSA) in 10/μg/ml AGP in counterbalance to the test wells which were incubated with 1 μg/ml bovine serum albumin (BSA) in 10/μg/ml AGP. Since HSA and BSA have essentially the same isoelectric point, it was surmised that HSA used in the same concentration in the control well as BSA (in the test well) would effectively serve as the noise balancing component. This was confirmed by demonstrating that test wells and their corresponding control wells had a noise balance ratio of unity when tested with a 1:2 (v/v) of nonimmune human sera (sera which had been preabsorbed for 30 minutes with 0.5% BSA, wt/v, at 37° C.).

For conduct of the assay, the procedure was generally as set forth above. Human sera were diluted 1:2 (v/v) in antigen buffer (see above) and preincubated in duplicate for 30 minutes at 37° C. with and without the addition of 0.75% BSA (wt/v) to the buffer.

Duplicate samples of normal serum were incubated for 1.5 hours at room temperature in test and control wells. The same samples absorbed with BSA were similarly incubated in the test wells. The general protocol: matrix coat, wash, block (PBS-T), wash, sample incubation, wash, detection with alkaline phosphatase labeled goat anti-human IgG fragments was as described in Example 3 above.

Figure 7:
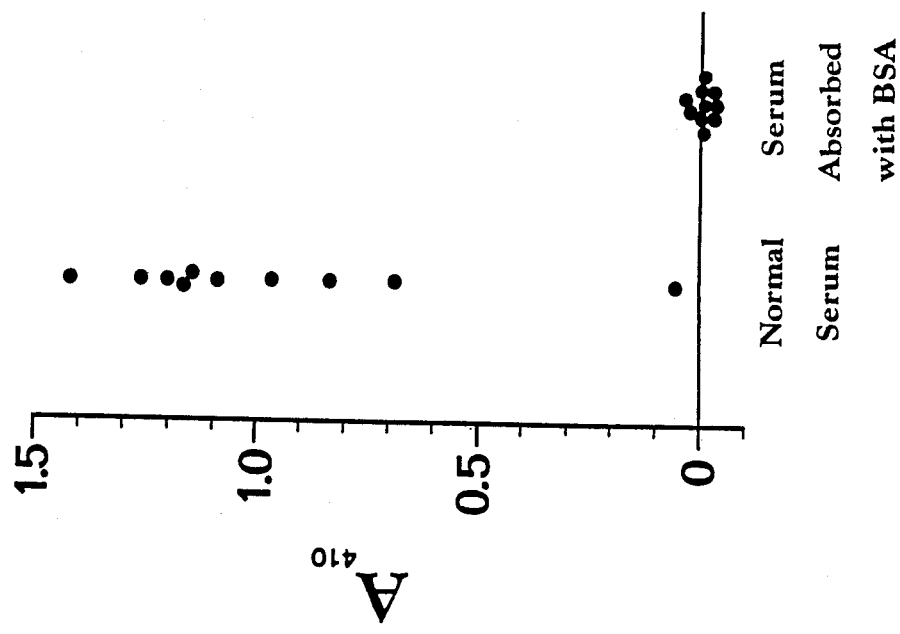
FIG. 7 shows the results of determination of antibody against BSA in various human serum samples.
Figure 9:
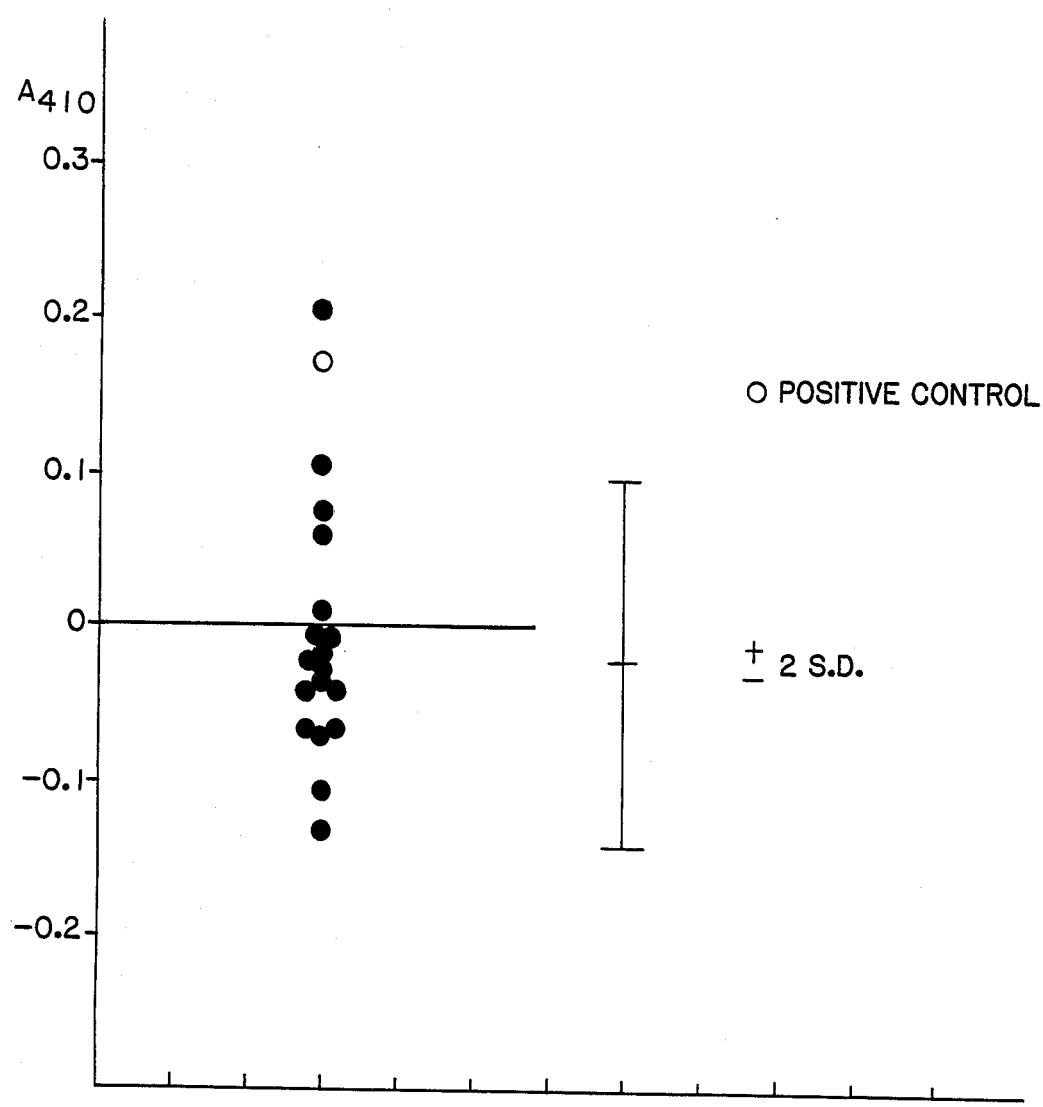
FIG. 9 shows the results of a matrix coat noise controlled assay for human antibody specific for p30.

Nine of the ten sera demonstrated significant levels of anti-BSA IgG as shown in section 1 of Table 3; however, incubation of the sera with BSA-containing buffer resulted in removal of the IgG and a cluster of null results (section 2 of Table 3). FIG. 7 shows a graphic representation of these results.

measured by an immunoassay with matrix coat noise control.

EXAMPLE 5

Development of an Alternative Matrix Composition

Because humans may exhibit antibodies to a wide variety of animal proteins due to dietary exposure (e.g., BSA, casein from cow's milk, gelatin, etc.), it may be desirable to eliminate nonhuman animal proteins from matrices in immunoassays which detect human antibodies to various antigens.

Therefore the procedure described above, and illustrated in Example 1, was used to determine a substitute matrix incorporating AGP and HSA for use in the detection of anti-p30 IgG in humans. As the optimum AGP concentration had already been determined (i.e., 10 μg/ml), it was necessary only to analyze tetrads with variable amounts of HSA.

Tetrads were organized as described in Example 1 containing 10 μg/ml of nondenatured human serum albumin (Calbiochem, San Diego, CA). Rabbit anti-p30 serum, diluted 1:999 (v/v) in antigen buffer containing 0.5% (wt/v) BSA was used as the positive control (containing target); nonimmune rabbit sera diluted 1:2 (v/v) to yield the same buffer concentration was used as negative control (containing no target). The protocol was as described above, using PBS-T blocking, and the diluted samples were incubated in the test and control wells for 1.5 hours at room temperature. The results are shown in FIG. 8.

The matrix composition containing 6 μg/ml HSA in addition to the 10 μg/ml of AGP appeared to be most favorable; this tetrad also had the noise balance ratio closest to unity (0.98).

EXAMPLE 6

Application of the HSA-Containing Matrix

The matrix composition shown to be optimum in Example 5 was used in performing the assay for anti-p30 in the serum of 18 women, using 1:3 (v/v) dilution of serum from subject F of Example 3 as a positive control. The procedure was exactly as described in Example 3, except for the nature of the matrix.

The results are shown in Table 4 and plotted in FIG. 8. The positive control and one subject (105) showed the presence of antibody; the remaining subjects gave a cluster of null results. The levels detectable are less than

TABLE 3

Detection of Anti-BSA IgG in Human Serum by Matrix Coat Noise-controlled ELISA

| Subject | 1 | 2 | 3 | 4 | 5 | 6 | 7 | 8 | 9 | 10 |
|---|---|---|---|---|---|---|---|---|---|---|
| ELISA for Anti-BSA IgG | | | | | | | | | | |
| Detecting Wells | 1.305 | 1.43 | 1.72 | 1.325 | 1.345 | 1.165 | 1.54 | 1.05 | 0.47 | 0.82 |
| Control Wells | 0.22 | 0.265 | 0.30 | 0.175 | 0.145 | 0.20 | 0.28 | 0.215 | 0.415 | 0.135 |
| Corrected Signal | 1.085 | 1.165 | 1.42 | 1.15 | 1.20 | 0.965 | 1.26 | 0.835 | 0.055 | 0.685 |
| ELISA for Anti-BSA IgG (Sera in detecting wells preincubated with 0.5% BSA) | | | | | | | | | | |
| Detecting Wells | 0.245 | 0.235 | 0.335 | 0.14 | 0.14 | 0.17 | 0.27 | 0.215 | 0.41 | 0.135 |
| Control Wells | 0.22 | 0.265 | 0.30 | 0.175 | 0.145 | 0.20 | 0.28 | 0.215 | 0.415 | 0.135 |
| Corrected Signal | 0.025 | −0.03 | 0.035 | −0.035 | −0.005 | −0.03 | −0.01 | 0.00 | −0.005 | 0.00 |

All values represent absorbance units at 410 nm.

These results show that anti-BSA antibody present in low concentrations in most human sera may contribute to false positive results in immunoassays which use BSA in a blocking step. These sera must therefore be preabsorbed with an excess of BSA to competitively inhibit binding of this antibody. As demonstrated here, these low levels of anti-BSA antibody in human sera can be 5 ng/ml. Again note the highly variable noise levels in these minimally diluted sera which often exceed the signal levels in the positive sera (see subjects 106, 107, and 128 in Table 4). Matrix coat noise control demonstrates the elevated signal levels in these sera to be due to background noise factors not related to the presence of target (anti-p30 IgG) in the samples.

TABLE 4

An ELISA to Detect Human IgG Antibody Specific for p30:
Results with a Matrix Coat Control Composed of Human Proteins Only

| ELISA with Matrix Coat Control | | | | | | | | | | |
|---|---|---|---|---|---|---|---|---|---|---|
| Subject | 101 | 102 | 105 | 106 | 107 | 108 | 109 | 111 | 112 | 113 |
| Detecting Well | .365 | .285 | .565 | .445 | .59 | .375 | .155 | .135 | .315 | .325 |
| Control Well | .265 | .35 | .36 | .515 | .695 | .315 | .195 | .175 | .24 | .33 |
| Corrected Signal | .10 | −.065 | .205 | −.07 | −.105 | .06 | −.04 | −.04 | .075 | −.005 |
| Subject | 114 | 115 | 116 | 118 | 119 | 126 | 128 | 129 | + | |
| Detecting Well | .43 | .305 | .265 | .22 | .145 | .22 | .48 | .255 | .455 | |
| Control Well | .56 | .325 | .33 | .225 | .18 | .21 | .495 | .28 | .285 | |
| Corrected Signal | −.13 | −.02 | −.065 | −.005 | −.035 | .01 | −.015 | −.025 | .17 | |

All values represent average absorbance units at 410 nm.

I claim:

1. A solid support for the conduct of immunoassay protocols at the surface of said support, wherein said support is coated with a matrix layer,
which matrix layer comprises an effective amount of both a noise reduction and a noise balancing component, wherein said noise reduction and noise balancing components are different from each other and different from any surface anti-target used in the immunoassay.

2. The support of claim 1 wherein the noise reduction component is a macromolecule having a pI below 6 and the noise balancing component is a macromolecule having a pI higher than that of said noise reduction component.

3. The support of claim 1 wherein the noise reduction component is selected from the group consisting of a polyamino acid, protein, glycoprotein, polysaccharide, glycolipid, and amphipathic macromolecules and wherein the noise-balancing component is selected from the group consisting of proteins, polypeptides, and amphiphatic macromolecules.

4. The support of claim 3 wherein the noise reduction component is α-acid glycoprotein (AGP) and the noise balancing component is selected from the group consisting of human and bovine serum albumin (HSA and BSA).

5. The support of claim 1 wherein the matrix layer is obtained by a process which comprises incubating the support with a solution containing about 4 μg/ml BSA.

6. The support of claim 4 wherein the matrix layer is obtained by a process which comprises incubating the support with a solution containing about 4 μg/ml BSA and about 10 μg/ml AGP.

7. The support of claim 1 wherein the matrix layer is obtained by a process which comprises incubating the support with a solution containing about 6 μg/ml HSA.

8. The support of claim 4 wherein the matrix layer is obtained by a process which comprises incubating the support with a solution containing about 6 μg/ml HSA and about 10 μg/ml AGP.

9. The support of claim 1 wherein a detecting portion of the surface further contains an effective amount of surface antitarget.

10. The support of claim 1 wherein the surface anti-target is the semen protein p30.

11. The support of claim 1 wherein the surface anti-target is BSA.

12. A method for preparing a solid support useful in an immunoassay, which comprises applying a matrix layer to said support, wherein said matrix layer contains an effective amount of both a noise reduction component and a noise balancing component, wherein said noise reduction and noise balancing components are different from each other and different from any surface anti-target used in the immunoassay.

13. The method of claim 12 wherein the matrix layer is applied as a solution containing an effective amount of a noise reduction component and a noise balancing component.

14. The method of claim 13 wherein the noise reduction component is a macromolecule having a pI below 6 and the noise balancing component is a macromolecule having a pI higher than that of said noise reduction component.

15. The method of claim 13 wherein the noise reduction component is selected from the group consisting of a polyamino acid, protein, glycoprotein, polysaccharide, glycolipid, and amphipathic macromolecules and wherein the noise-balancing component is selected from the group consisting of proteins, polypeptides, and amphiphatic macromolecules.

16. The method of claim 13 wherein the noise reduction component is α-acid glycoprotein (AGP) and the noise balancing component is selected from the group consisting of human and bovine serum albumin (HSA and BSA).

17. The method of claim 13 wherein the matrix layer is obtained by a process which comprises incubating the support with a solution containing about 4 μg/ml BSA.

18. The method of claim 13 wherein the matrix layer is obtained by a process which comprises incubating the support with a solution containing about 4 μg/ml BSA and about 10 μg/ml AGP.

19. The method of claim 13 wherein the matrix layer is obtained by a process which comprises incubating the support with a solution containing about 6 μg/ml HSA.

20. The method of claim 13 wherein the matrix layer is obtained by a process which comprises incubating the support with a solution containing about 6 μg/ml HSA and about 10 μg/ml AGP.

21. The method of claim 13 wherein the support is coated in control surface portions with matrix layer alone and in test portions with matrix layer and with an effective amount of surface antitarget.

22. The method of claim 21 wherein the test portions are coated with an admixture of the surface antitarget and the matrix layer.

23. The method of claim 21 wherein the test portions are coated first with matrix layer and subsequently with surface antitarget.

24. The method of claim 21 wherein the test portions are coated with surface antitarget and then with matrix layer.

25. A method to eliminate false positives in solid-supported immunoassays, which method comprises conducting said immunoassays with a protocol which includes the step of contacting a sample or reagent with the solid support of claim 1.

26. A method of optimizing the composition of a matrix layer effective in improving the results of a solid support immunoassay, which comprises determining the matrix index for a variety of matrix layer compositions and selecting the composition with the highest matrix index.

27. A method of optimizing the composition of a matrix layer effective in improving the results of a solid supported immunoassay which comprises determining the noise balance ratio for a series of matrix compositions and selecting the composition with the noise balance ratio closest to unity.

28. A solid support suitable for determining the relative noise reduction capabilities of at least two macromolecules of varying isoelectric points for the assay of a desired target, which comprises a solid support containing a series of test regions, which test regions contain, in series, each of said candidate macromolecules of varying isoelectric points.

29. A method for selecting a candidate noise reduction component for a solid phase immunoassay which comprises applying a concentrated form of a biological sample to be assayed lacking target to the solid support of claim 28 and measuring the relative amounts of non-specific binding in each region of the series of test regions.

30. A method of conducting a solid phase immunoassay which comprises applying a sample to be tested for target substance to solid support containing control surface portions and test portions wherein the control surface portions contain a matrix layer comprising at least one of an effective amount of noise reduction component and an effective amount of noise balancing component, and wherein the test portions contain said matrix layer in admixture with an effective amount of surface antitarget;

washing the support;

treating the support with detecting antitarget;

washing said support, and detecting the presence or absence of detecting antitarget on the support.

31. The method of claim 30 which further includes blocking the support with a detergent or with a detergent plus protein mixture before treating the support with sample.

* * * * *